(12) United States Patent
Hashimoto et al.

(10) Patent No.: US 6,676,374 B2
(45) Date of Patent: Jan. 13, 2004

(54) AIR-DRIVEN ROTATING AND CUTTING DEVICE FOR USE IN MEDICAL AND DENTAL PROCEDURES

(75) Inventors: Nobuo Hashimoto, Kyoto (JP); Yoshihiko Kinoshita, Kyoto (JP); Minoru Hayashida, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 28 days.

(21) Appl. No.: 09/729,150

(22) Filed: Dec. 1, 2000

(65) Prior Publication Data

US 2001/0002975 A1 Jun. 7, 2001

(30) Foreign Application Priority Data

Dec. 3, 1999 (JP) .............................. 11-344906

(51) Int. Cl.[7] .............................. A61C 1/05; F03B 13/04
(52) U.S. Cl. ...................................... 415/904; 433/132
(58) Field of Search ................................. 415/904, 202, 415/198.1, 224; 433/132

(56) References Cited

U.S. PATENT DOCUMENTS

| 3,386,702 A | * | 6/1968 | Krzyszczuk | ................. 415/904 |
| 4,146,964 A | * | 4/1979 | Lares et al. | ................. 415/904 |
| 5,902,108 A | * | 5/1999 | Nakayama et al. | ......... 415/904 |

* cited by examiner

*Primary Examiner*—Edward K. Look
*Assistant Examiner*—Igor Kershteyn
(74) *Attorney, Agent, or Firm*—Koda & Androlia

(57) ABSTRACT

An air-driven rotating and cutting device or handpiece has a double-wheel rotor. The handpiece includes connecting channels for guiding air from first turbine blades to second turbine blades. Each of the channels is defined by an opening opened toward a direction parallel to the rotational axis and a surface portion formed by extending the opening to a direction along the rotational axis.

21 Claims, 16 Drawing Sheets

AIR-DRIVEN ROTATING AND CUTTING DEVICE FOR USE IN MEDICAL AND DENTAL PROCEDURES

The present invention relates to an apparatus for rotating a cutting tool by the use of a pressurized-air. Also, the present invention relates to an apparatus for an air-driven rotating and cutting device such as drill used in medical and dental procedures and machine workings.

BACKGROUND OF THE INVENTION

Japanese Patent Application JP 10-123746 (A) filed in the name of J. Morita MFG. Cooperation discloses an air-driven rotating and cutting device, or handpiece, for the medical and dental procedures and machine workings. The device employs a double-wheel rotor for effectively changing a pneumatic energy into a rotational force. The double-wheel rotor has a hub in the form of ring that is defined at an outer periphery thereof with first and second turbine wheels. The first turbine blade includes a plurality of first turbine blades each extending radially and outwardly from the center of the hub. Likewise, the second turbine wheel has a plurality of second turbine blades each extending radially and outwardly from the center of the hub.

The handpiece is formed at its head with a chamber in which an inner housing with an outer configuration in the form of cylinder and corresponding to an inner configuration of the chamber is received. In turn, the inner housing receives the rotor and a bearing mechanism for rotatably supporting the rotor. The head and the inner housing are formed with an air-supply passage for ejecting a compressed air toward the first turbine wheel of the rotor and an air-discharge passage for discharging the air from the second turbine wheel. Also, the inner housing is formed with a connecting passage for guiding the pressurized-air from the first turbine wheel to the second turbine wheel. This allows that the pressurized-air ejected from the supply passage impinges on the first turbine blades of the first turbine wheel. Then, the pressurized-air travels through the connecting passage to the second turbine wheel where it also impinges on the second turbine blades and then discharged through the discharge passage to the atmosphere.

As described above, the handpiece with the double-wheel rotor allows the energy of the pressurized-air to be used most effectively at the two turbine wheels. This results in that the drill can be rotated in a high speed with an elevated torque feature than the conventional handpiece with a single-step rotor.

In this handpiece with double-wheel rotor the cylindrical part of the inner housing has a plurality of slots formed in its certain peripheral area for defining the connecting passages of the inner housing. Also, the slots are closed at outer openings thereof by a closure in the form of ring that surrounds the inner housing. Disadvantageously, the arrangement needs the additional closure or ring. In addition, in order to secure the ring to the cylindrical housing, screw threads should be machined in the opposing outer and inner surfaces of the cylindrical housing and the ring, respectively. Besides, a possible gap between the cylindrical housing and the ring results in a leakage of the pressurized-air, deteriorating the effective use of the energy derived from the pressurized-air and then the stability in the rotational number and the torque of the rotor.

Indeed, the handpiece results in the higher torque even at the high rotational number. This means that the double-wheel rotor is the most effective device for the dental handpiece that is required to rotate the cutting tool at about 300,000 to 500,000 rpm. On the other hand, another requirement has been existed to slightly decrease the rotational number while maintaining the high torque.

For example, for the dental handpiece, a slight decrease of the rotational number will result in various advantages. For example, heat generated at the cutting of the tooth is decreased, which is effective for cushioning a toothache possibly caused by the heat and also avoiding pulpitis possibly caused by the heat increase of the pulp. Also, noises generated at the cutting are decreased and the noises with higher frequencies are also reduced. In particular, the noises generated by the rotations of the rotor and cutting tool at the procedure, in particular noises with high frequency, may provide the patient with a fear against the procedure. Further, the high speed rotation, for example, at about 300,000 to 500,000 rpm, may damage the elongated dental cutting tool even by a slight increase of the load at the cutting of the tooth. On the contrary, a possibility of the damage will be reduced considerably even by a slight decrease of the rotational number, for example, 10,000 to 50,000 rpm. Furthermore, a slight decrease of the rotational number of the cutting tool, for example, from about 300,000–500,000 rpm by about 10,000–50,000 rpm, results in a considerable extension of a durability of a bearing mechanism, in particular ball bearing, of the dental cutting tool.

In addition, in the above-described double-wheel rotor the first and second turbine wheels are positioned along the central axis of the rotor, which results in the enlargement in size of the head of the handpiece in that direction. However, the size of the head in that direction is restricted in the handpieces for children and aged persons. This requires another technique to be developed to realize the high speed and high torque handpiece with small head incorporated with the double-wheel rotor.

Besides, in the handpiece with double-wheel rotor the passage for the supply of air to the rotor is defined by a plurality of parts. This requires a variety of parts to be prepared and then assembled together in the manufacturing of the handpiece. This also causes small gaps between the neighboring parts, which result in a leakage of the pressurized-air and also a deterioration of effectiveness in the energy change of the pressurized-air into the rotation of the rotor.

SUMMARY OF THE INVENTION

Accordingly, an air-driven rotating and cutting device comprises a rotor having a rotational axis and detachably holding a cutting tool in the rotational axis. The rotor is formed with first and second turbine wheels. The first and second turbine wheels are formed with first and second blades, respectively. Also, each of the first blades defines a first channel with adjacent first blade therebetween and each of the second blades defines a second channel with adjacent second blade therebetween. The device further includes a housing for receiving the rotor for rotation about the rotational axis. The housing has channels for fluidly connecting the first and second channels, so that an air is guided from the first channels through the connecting channels to the second channels as the rotor rotates. Further, each of the connecting channels is defined by an opening opened toward a direction parallel to the rotational axis and a surface portion formed by extending the opening to a direction along the rotational axis.

With the arrangement, the connecting channels are formed or machined only from the direction parallel to the rotational direction without tilting or changing working direction, causing the head with the connecting channels to be manufactured without any difficulty and thereby inexpensively. The conventional housing has slots extending between the inner and outer surfaces, which decreases the strength of the housing as well as the durability thereof. Contrary to this, according to the present invention, since the housing is free from such slots, it has a greater strength than the conventional one. Also, the connecting channel in the conventional device is formed by two separate members (i.e., inner housing and the ring) which should be assembled together. However, the connecting channels in the device of the present invention are formed in the single member. This causes the device to be manufactured more easily and prevents the pressurized air from leaking, which stabilizes the rotational number and the torque of the rotor.

BRIEF DESCRIPTION OF THE DRAWINGS

It should be noted that like parts are designated by like reference numerals throughout the drawings.

DETAILED DESCRIPTION OF THE PREFERRED EMBODIMENTS

With reference to the drawings, preferred embodiments of the present invention will be described hereinafter. It should be noted that the following description relates to specific embodiments in each of which the present invention is applied to a dental, air-driven, rotating and cutting device (hereinafter referred to as "handpiece"). However, the present invention is not limited thereto and equally applied to surgical instruments and another devices for the fabrication of working materials and parts.

I. First Embodiment

Figure 1:
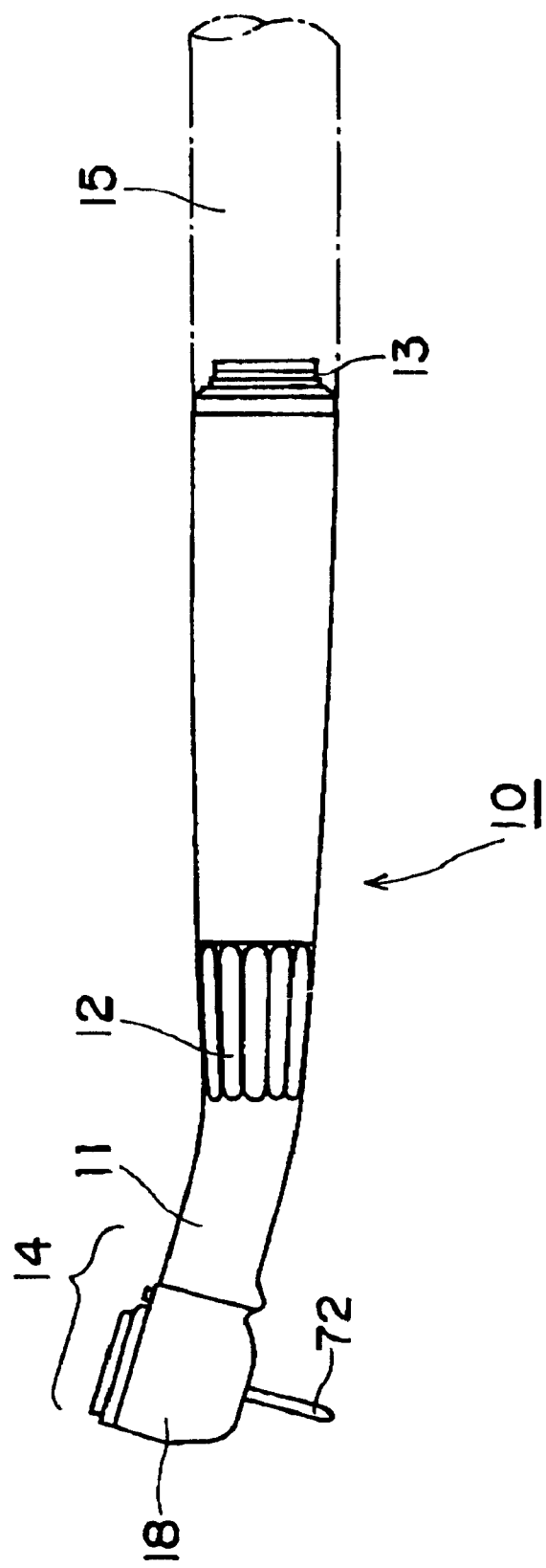
FIG. 1 is a side elevational view of an air-driven rotating and cutting device (handpiece) of the present invention.

FIG. 1 shows a side elevational view of the handpiece according to the embodiment of the present invention. In this drawing, the handpiece generally indicated by reference numeral 10 has a grip portion 12 that is gripped by an operator at a dental treatment. The grip portion 12, like conventional handpieces, has a connecting portion 13 at one end thereof for the connection of a supply tube 15 through which a hydraulic fluid such as air and water is supplied. The other end of the grip portion 12 is integrated with a neck portion 11 and a head portion 14 away from the grip portion 12. The head portion 14 receives a cutting tool 72 so that the cutting tool 72 can be detached as necessary.

FIGS. 2–6 shows the enlarged sectional views of the head 14. As shown in the drawings, the head portion 14 is integrally formed with a coupling portion 16 positioned at the distal end of the grip portion 12 and a cylindrical housing 18 in which a cutting tool 72 and a drive mechanism 70 for driving the cutting tool 72 are received. In particular, the cylindrical housing 18 is directed so that a central axis indicated by an imaginary line 22 crosses substantially perpendicular to a central axis of the coupling portion 16, also indicated by an imaginary line 20. Since the central axis 22 corresponds to a rotational axis of the cutting tool which will be described hereinafter, it is referred to as "rotational axis" hereinafter, as necessary.

Figure 2:
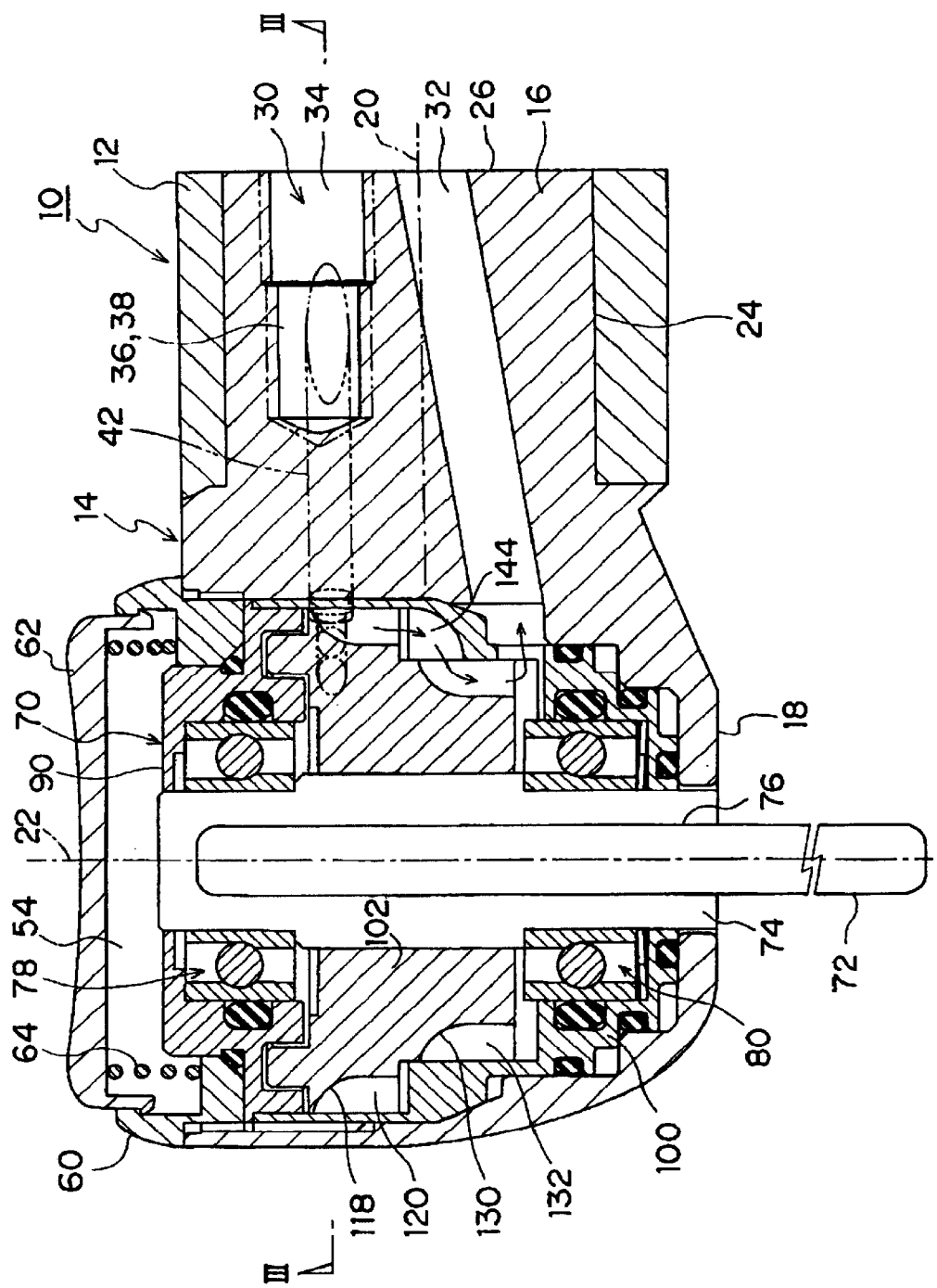
FIG. 2 is an enlarged cross sectional view of the device according to the first embodiment of the present invention.
Figure 3:
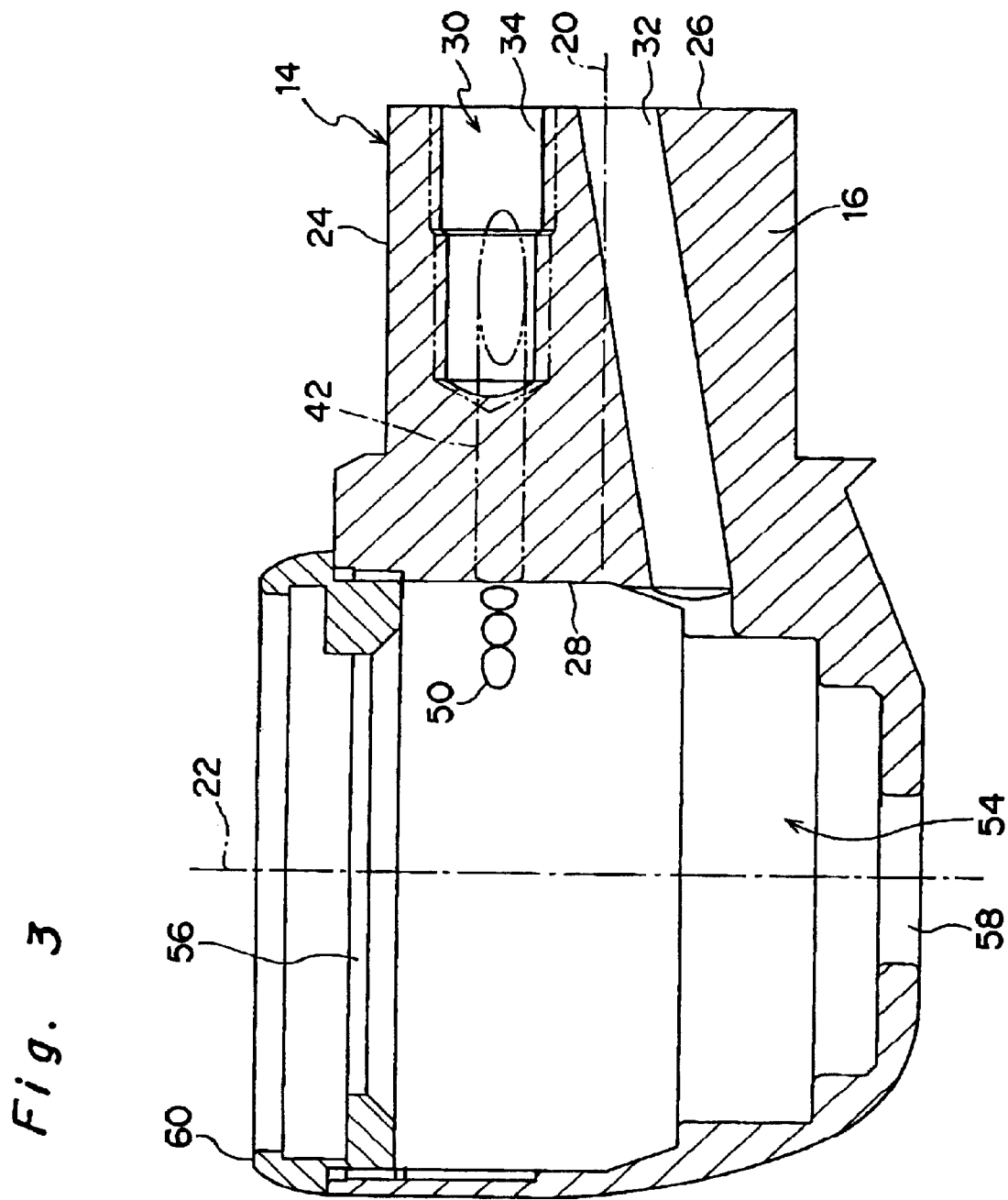
FIG. 3 is a cross sectional view of a head shown in FIG. 2.

As best shown in FIG. 2, the coupling portion 16 of the head portion 14 has a reduced portion 24 which is sized and shaped so that it can be detachably inserted in a corresponding hole formed at the distal portion of the cylindrical grip portion 12. Also, as best shown in FIG. 3, the coupling portion 16 is formed with a plurality of holes extending and fluidly connecting between a rear end surface 26 (right side end surface in the drawing) facing to the grip portion 12 and a front end surface (left side end surface) facing to an inner chamber 54 defined and surrounded by the cylindrical housing 18. The holes include a supply passage 30 through which a pressurized air is supplied to a mechanism 70 that drives the cutting tool and a discharge passage 32 through which the pressurized air from the drive mechanism 70 is discharged.

Figure 4:
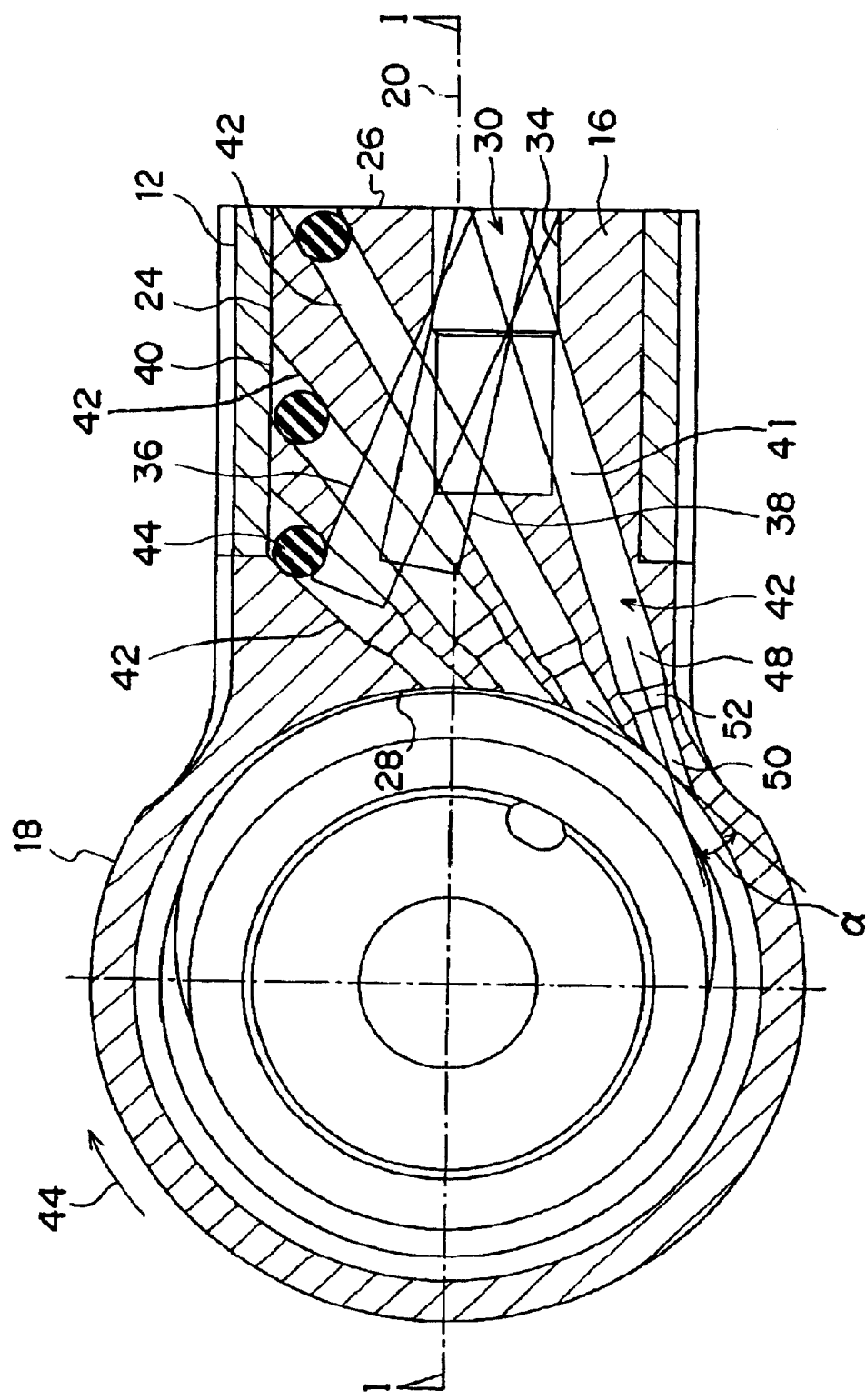
FIG. 4 is a cross sectional view of the handpiece taken along a line III—III in FIG. 2.

The supply passage 30 is fluidly connected at its rear end to a conduit or pipe positioned in and along the longitudinal direction of the grip portion 12 and extending backward from the connecting portion 13 of the supply tube 15 shown in FIG. 1. As best shown in FIG. 4, the distal end of the supply passage 30 is formed by drilling from the rear end surface 26 adjacent to the grip portion 12 and from a peripheral surface of the reduced portion 24. Specifically, referring to FIG. 4, a main supply passage 34 is drilled from the rear surface 26 and extended parallel to the grip axis 20. Next, one or more intermediate supply passages 36 and 38 are drilled at the inner surface of the main supply passage and extended along a plane (supply level) which lies perpendicular to the rotational axis 22 and on the central axis of the main supply passage 34. Before or after the formation of the intermediate supply passages 36 and 38, a plurality of passages 41 serving as supply nozzles 42 are formed from the outer peripheral surface 40 of the reduced portion 24 and from the inner surface of the main supply passage 34 and, if necessary, the rear end surface 26 so that they cross the intermediate supply passages 36 and 38 or the main supply passage 34 and then open at the front end surface 28 of the coupling portion. This allows that the pressurized air is supplied from the supply tube 15 through the connecting portion 13 connected thereto to the rear opening of the main supply passage 34. Also, each of the supply nozzles 42 formed from the outer periphery 40 of the reduced portion 24 is closed in a sealing fashion by a sealing ball such as steel ball 44 forced therein. Further, the nozzles 42 are positioned so that each of nozzles 42 defines a greater angle with said central axis 20 of the coupling portion 16 than another nozzle 42 located on a downstream side with respect to the rotational direction 44 of said rotor 102.

Preferably, the air supply nozzles 42 are directed so that the cutting tool received in the cylindrical housing 18 is rotated by the pressurized-air ejected from the supply nozzles 42 about the rotational axis 22 in a direction indicated by an arrow 44 (i.e., in the clockwise direction in FIG. 4).

More preferably, as shown in FIG. 4, each of the supply nozzles 42 is designed so that its longitudinal axis defines an angle (nozzle angle) α of about 10 to 50 degrees with a tangential line extending through a crossing point of the inner surface of the cylindrical housing 18 and the longitudinal axis supply nozzle.

Advantageously, each of the supply nozzles 42 is formed with a portion 52 tapering toward the inner surface 28 at a portion spaced a certain distance away from the surface 28 so that an overall opening area at the connections to the intermediate supply passages 36 and 38 is greater than that of throats 50 opened at the surface 28.

More advantageously, an effective area corresponding to an overall area of the throats 50 is smaller than an effective area of the main supply passage 34 and also another effective area of the intermediate supply passages 36 and 38. It should be noted that where one of the intermediate supply passages 36 and 38 shares in part the other, the effective area of the intermediate passages 36 and 38 are determined by subtracting the shared area from the sum of the respective areas.

Figure 6:
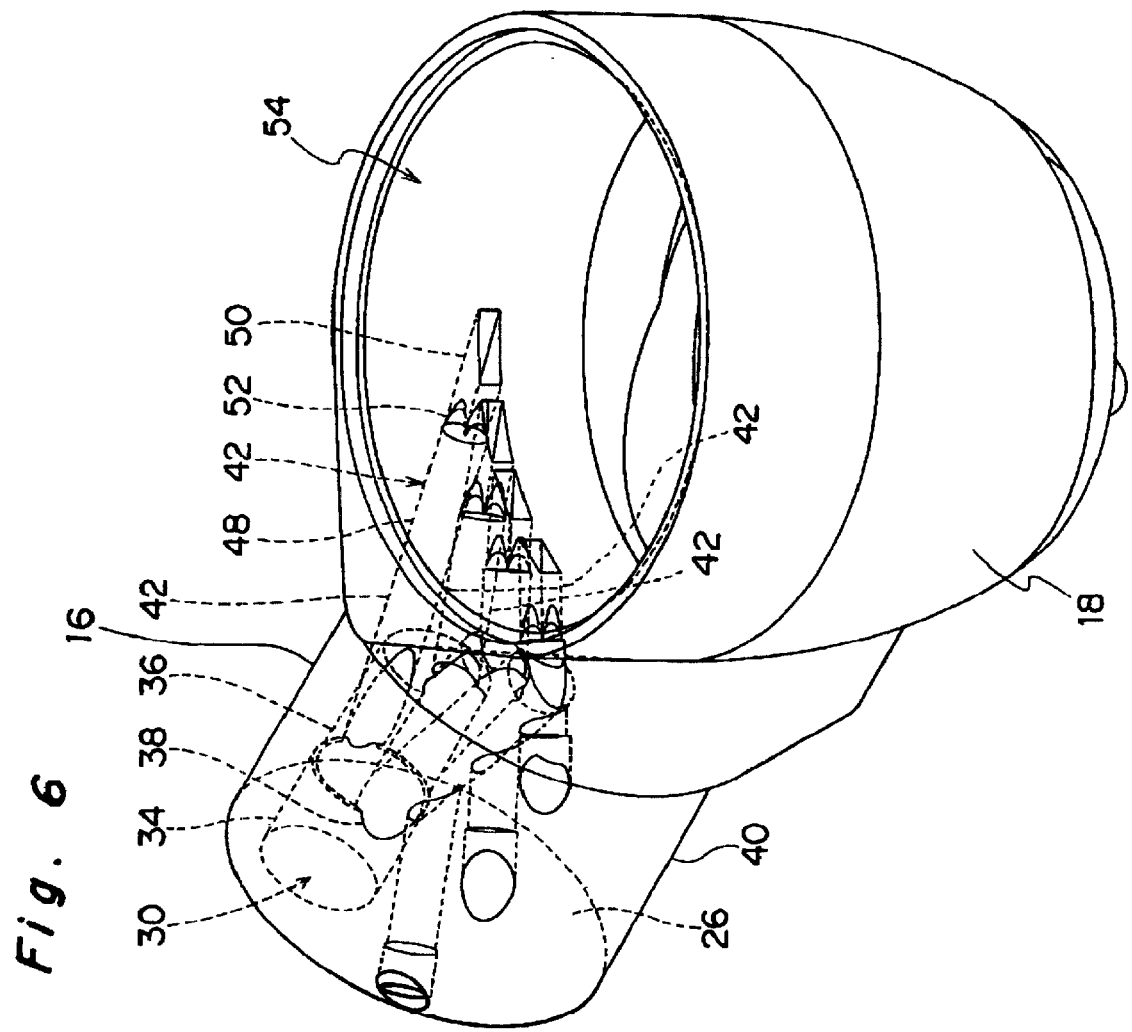
FIG. 6 is a perspective view of the head according to another embodiment.

Although the cross sectional configuration of the supply nozzle 42, i.e., throat 50, is in the form of circle, it is not limited thereto and may be in the form of rectangular as shown in FIG. 6.

Figure 5:
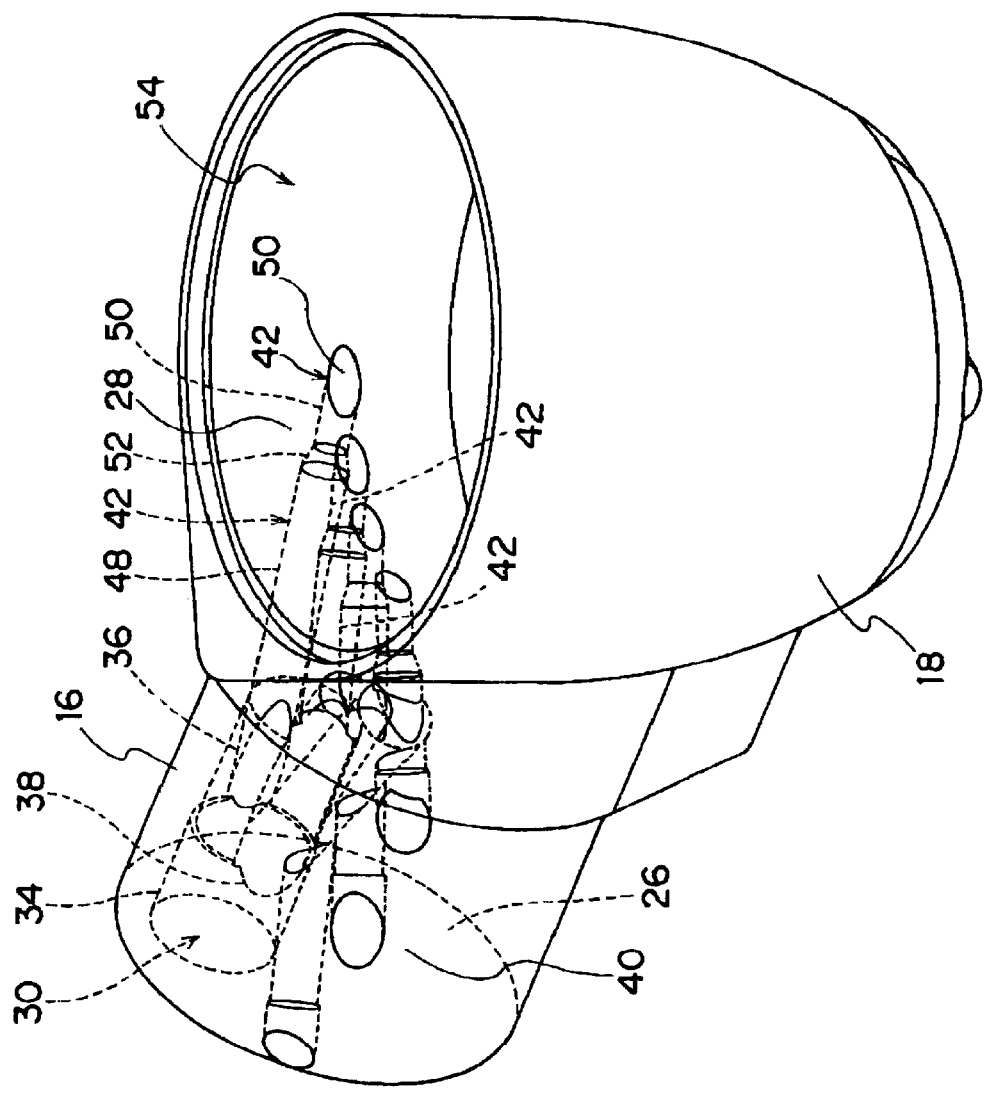
FIG. 5 is a perspective view of the head shown in FIG. 2.

Also, in this embodiment the main supply passage 34 is extended parallel to the grip axis 20 of the coupling portion 14. This is advantageous for an effective use of a space adjacent to the rear end surface 26, compared to where the main supply passage is angled to the grip axis 20. Also, as shown in FIGS. 5 and 6, this allows the nozzles to be formed perpendicular to the rotational axis 22 more easily.

As best shown in FIGS. 2 and 3, the discharge passage 32, which is positioned below the supply passages, is defined by a through-hole extending from the rear end surface 26 to the front end surface 28 of the coupling portion.

As best shown in FIGS. 2 and 3, the cylindrical housing 18 of the head portion 14 has a cylindrical chamber 54 formed therein. The chamber 54 has a specific size and configuration corresponding to the outer configuration of the drive mechanism 70 that uses the pressurized air from the supply passage 30 as a rotational force of the cutting tool. The chamber 54 is opened at its top and bottom openings 56 and 58 so that the drive mechanism 70 is received therein through the top opening 56. The drive mechanism 70 has a tool holder 74 for detachably holding the cutting tool 72 provided through the bottom opening 58. To protect the driving mechanism 70 positioned in the chamber 54, the top opening 56 has a releasable cap support ring 60 to which a cap 62 (see FIG. 6) is detachably mounted. In this embodiment, as shown in FIG. 1, a biasing spring 64 is positioned in an interior of the cap 62 so that the cap 62 is positively maintained in the position shown in the drawing by the biasing force of the spring 64. The cap 62 is mechanically connected to the tool holder 74 so that once the cap 62 is pushed down the tool holder 74 releases the cutting tool for the exchange thereof.

Figure 7:
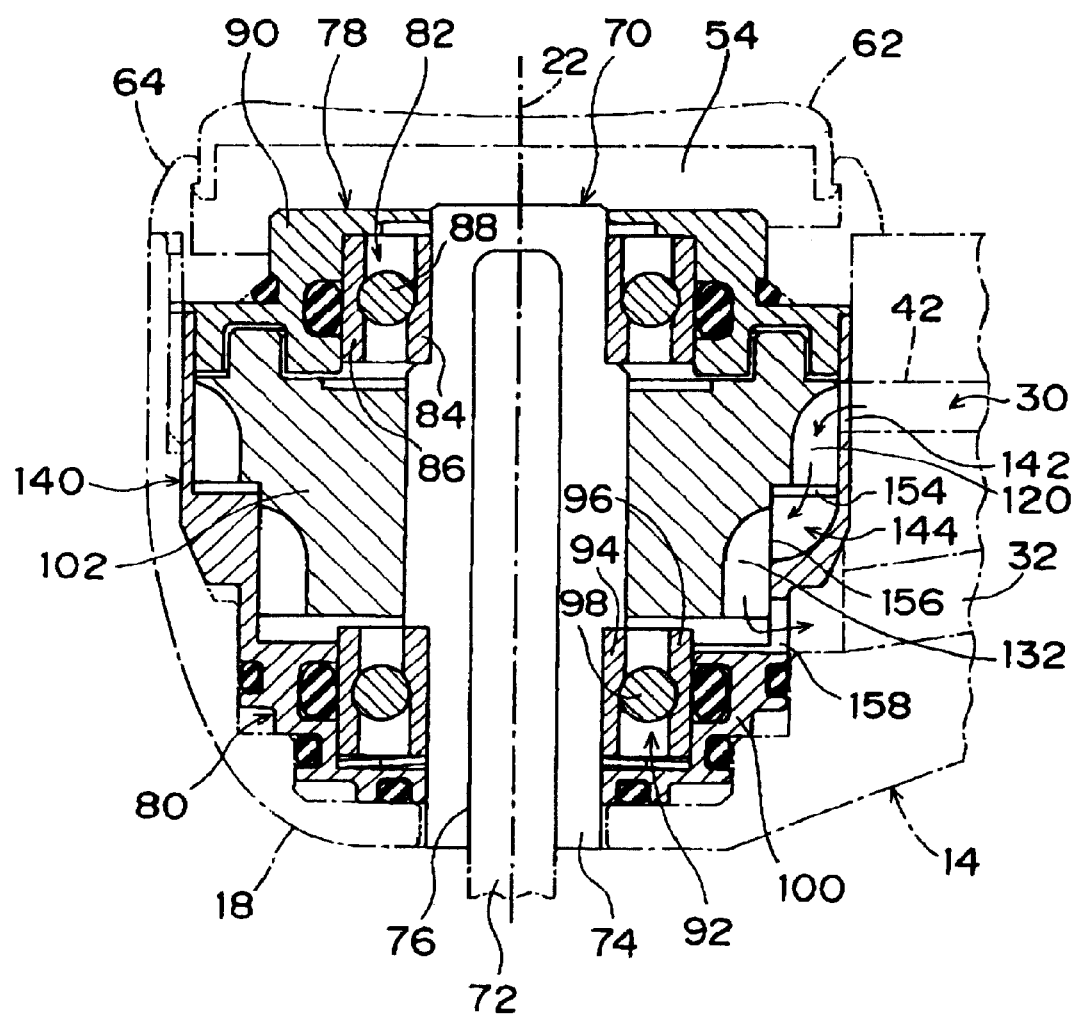
FIG. 7 is a cross sectional view of a drive mechanism of the handpiece shown in FIG. 2.

As best shown in FIGS. 2 and 7, the drive mechanism 70 for driving the cutting tool 72 has the tool holder 74 for holding the cutting tool 72 in the rotational axis 22 of the chamber 54. The tool holder 74 has a hole (tool support hole) 76 formed therein and extended from one end portion (i.e., lower portion in FIG. 6). Also, the tool holder 74 has a chuck mechanism not shown for holding the cutting tool 72 inserted and positioned in the tool support hole 76. The chuck mechanism, which may be made of conventional chuck mechanism, is designed so that when the cap 62 is pushed down from its original position the chuck mechanism unlocks the cutting tool 72 for the exchange thereof and when the cap 62 is maintained in the original position the chuck mechanism locks the cutting tool 72.

As best shown in FIGS. 2 and 7, the tool holder 74 is supported for rotation about the rotational axis 22 by the upper and lower bearings 78 and 80 provided above and below the tool holder. The upper and lower bearings 78 and 80 have the same structure and, in this embodiment, are made of ball bearings. The bearing may be another type of bearing such as slide bearing and fluid (air) bearing.

Specifically, the ball bearing 82 of the upper bearing 78 has an inner ring 84, an outer ring 86 positioned in an coaxial fashion with the inner ring 84, and a number of balls 88 positioned between the inner and outer rings. The inner ring 86 is secured around the tool holder 74. The outer ring 86, on the other hand, is secured to an upper casing 90 inserted in the chamber 54 of the cylindrical housing 18. The upper housing 90 is made of ring-like member having an outer configuration corresponding to the inner configuration of a part of the chamber where the upper housing 90 is received. A peripheral portion of the ring-like member has one or more stops or projections that, when the upper casing 90 is inserted in the chamber 54, engages with corresponding stops (e.g., grooves extending parallel to the rotational axis) formed in the inner surface defining the chamber 54 therein, preventing the rotation of the upper casing 90 in the chamber 54. Although not shown, opposing portions of the outer ring 86 and the upper casing 90 are formed with similar stops to prevent the relative rotation thereof. Also, if necessary, a suitable sealing structure such as packing made of rubber is provided between, for example, the upper casing 90 and the outer ring 86, the upper casing 90 and the cap support ring 64, and the upper casing 90 and the cylindrical housing 18 to prevent the leakage of the pressurized air.

In general, the lower bearing 80 has the same structure as the upper bearing 78. Specifically, the ball bearing 92 of the lower bearing 80, similar to the ball bearing 82 of the upper bearing 78, is made of an inner ring 94, an outer ring, and a number of balls 98 positioned between the inner and outer rings. The inner ring 94 is secured around the tool holder 74.

The outer ring 96, on the other hand, is secured to a lower casing 100. The lower casing 100 is made of ring-like member having an outer configuration that corresponds to a part of the inner configuration of the chamber where the lower casing and the rotor are received. The outer surface of the lower casing 100 and the inner surface of the chamber 54 are formed with respective stops that engages with each other in order to prevent the rotation of the lower casing 100 relative to the cylindrical housing 18. For example, the stops are made of one or more grooves formed in the chamber 54 and projections formed in the lower casing 100. If necessary, a suitable seal structure such as packing made of rubber is provided between the neighboring members, for example, the lower casing 100 and the cylindrical housing 18, and the lower casing 100 and the housing 18 to prevent the leakage of the pressurized air.

Referring again to FIGS. 2 and 7, the double-wheel rotor 102 is provided between the upper and lower bearings 78 and 80 to rotate the tool holder 74 and then the cutting tool 72 by the use of the pressure of air ejected from the supply passage 30. As shown in detail in FIG. 8, the rotor 102 is made of a ring-like member having a central through-hole 104 formed therein. An inner diameter of the through-hole 104 is substantially equal to an outer diameter of a mid-portion of the tool holder 74 that holds the rotor 10. A hub 106 defining the though-hole 104 therein has an upper, first turbine wheel 108 and a lower, second turbine wheel 122.

The first turbine wheel 108 has a circular upper wall 110 extending radially and outwardly from the top end of the hub 106, and a number of (e.g., eighteen) projections or first turbine blades 112 each extending downwardly from the bottom surface of the upper wall 110 and radially outwardly from the peripheral surface of the hub 106. The first turbine blades 112 are equally spaced along the periphery of the hub 106. Formed between the neighboring first turbine blades 112 is a first air channel 120 which is defined by three surfaces; one side surface of one blade (i.e., active surface 114 located upstream side with respect to the rotational direction of the rotor 102), the opposing side surface of the neighboring blade (i.e., guide surface 116 located downstream side with respect to the rotational direction of the rotor), and a peripheral surface portion 118 of the hub between the opposing active and guide surfaces. The position of the first air channel 120 in a direction parallel to the rotational axis is determined so that, when the rotor 102 is positioned in the chamber 54, the pressurized-air ejected from the supply nozzles 42 is guided into an upper portion of respective air channels 120. The peripheral surface portion 118 of the hub 106 is curved downwardly from the outer peripheral edge of the upper wall 110, which is best shown in FIG. 2, so that the pressurized air ejected into the channel 120 travels downwardly along the curved surface 118 with the minimum friction therewith. Also, as can be seen from FIG. 8 each of the turbine blades 112 is extended from the upper wall 110 so that it is inclined a bit toward the downstream side with respect to the rotational direction 44 of the rotor 102 and then turned at its intermediate portion toward the upstream side.

The second turbine wheel 122 has a lower wall 123 of which peripheral edge is defined by the innermost bottom edges of the first channels 120 and a number of (e.g., eighteen) equally spaced projections or second turbine blades 124 straightly extending downwardly from a bottom surface of the lower wall 123 and radially outwardly from the peripheral surface of the hub 106. As a result, a second channel 132 is formed between each of the neighboring second turbine blades 124. Specifically, the second channel 132 is defined by three surfaces; one side surface of one blade (i.e., active surface 126 located upstream side with respect to the rotational direction of the rotor 102), the opposing side surface of the neighboring blade (i.e., guide surface 128 located downstream side with respect to the rotational direction of the rotor), and a peripheral surface portion 130 of the hub between the opposing active and guide surfaces. The peripheral surface portion 130 of the hub 106, defining in part the second channel 132, is curved inwardly downwardly from the outer peripheral edge of the upper wall 123, which is best shown in FIG. 2, so that the pressurized air ejected into the channel 132 is directed downwardly along the curved surface 130 with the minimum friction therewith. Also, the second channel 132 is positioned so that, when the rotor 102 is mounted in the chamber 54, the lowermost end opening of the channel 132 takes substantially the same level as the discharge passage 32.

Figure 8:
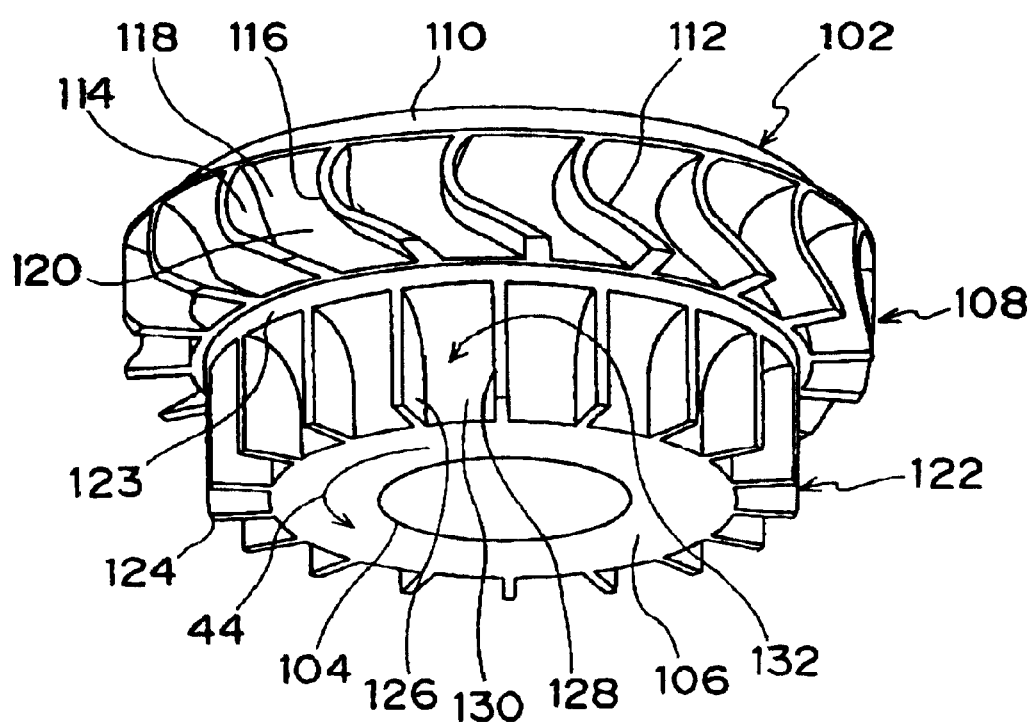
FIG. 8 is a perspective view of the rotor in the handpiece shown in FIG. 2.

As best shown in FIG. 8, the first channels 120 are displaced in the rotational direction 44 of the rotor 102 relative to second channels 132. Specifically, the lowermost end openings of the first channels 120 are shifted from the uppermost end openings of the second channels 132 with respect to the rotational direction of the rotor 102.

Also, in the rotor 102 so constructed the second turbine blades 124 and the second channels 132 are directed parallel to the rotational axis 22, which allows the second turbine blades and the second channels 132 to be machined only from the direction parallel to the rotational axis 22. This ensures that the rotor can be manufactured more easily and inexpensively than the conventional rotor in which both the first and second turbine blades are curved.

Referring to FIG. 7, an air guide ring 140 or inner housing is positioned around the rotor 102. The guide ring 140 defines another connecting channels 144, each of which serves as a guide portion for guiding the pressurized air from the supply passage 30 radially inwardly into the first channels 120 and then from the first channels 120 into the second channels 132. Although the guide ring 140 is formed integrally with the lower casing 100, it may be made separately from the lower casing. Also, the guide ring 140 may be integrated in the head portion 14. In this instance, an inner surface portion of the guide ring 140 defines a part of chamber 54. This structure allows the guide ring to be molded together with the head inexpensively by the use of a suitable resin or sintered metal.

Figure 9:
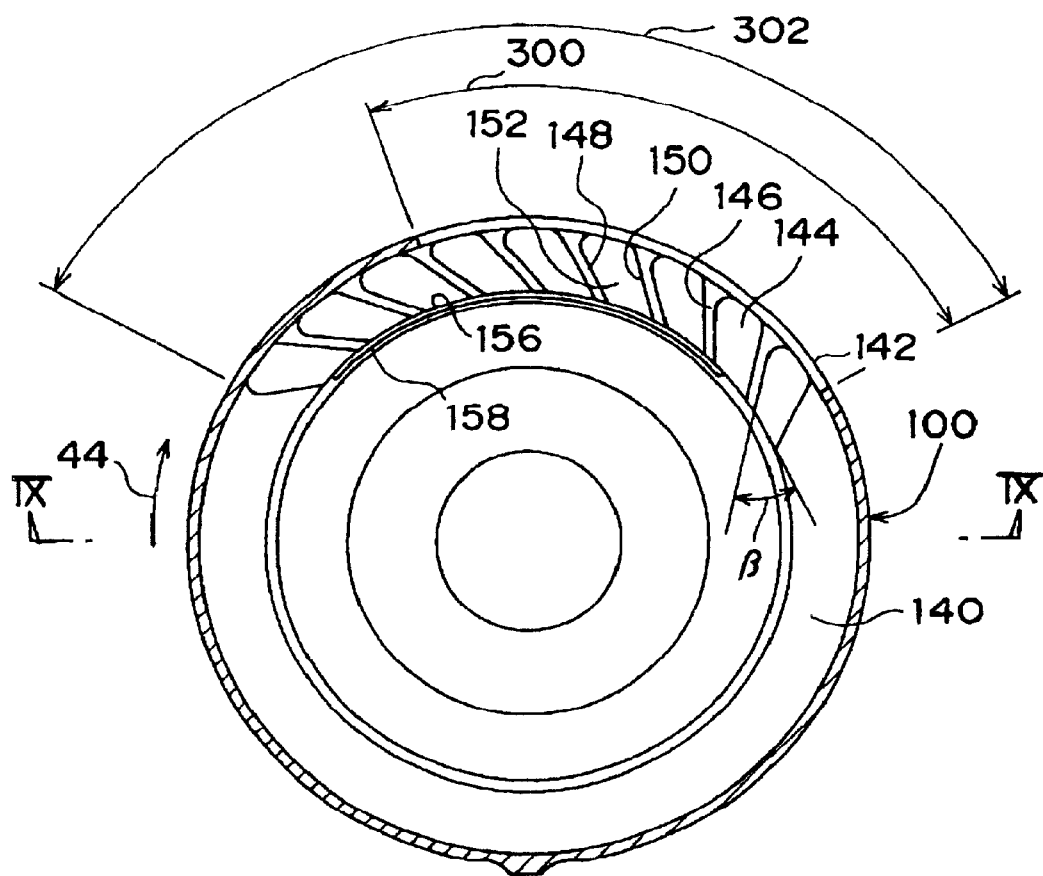
FIG. 9 is a cross sectional view of the guide ring for use with the handpiece shown in FIG. 2, taken along a line VIII—VIII in FIG. 10.
Figure 10:
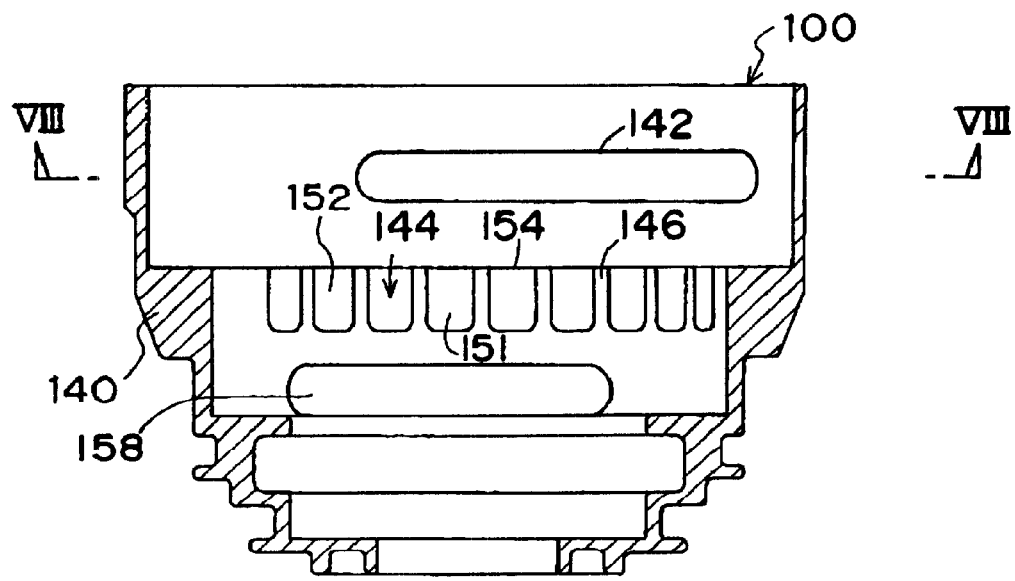
FIG. 10 is a cross sectional view of the guide ring for use with the handpiece shown in FIG. 2, taken along a line IX—IX in FIG. 9.

The lower casing 100 with the guide ring 140 has an inlet 142 in an area 300 to which, when the lower casing 100 is located in a predetermined position of the chamber 54, the supply nozzles 42 of the supply passage 30 oppose, so that the pressurized air ejected from the supply nozzles 42 is fed radially inwardly from the inlet 142 into the first channels 120. As shown in FIGS. 9 and 10, the inlet 142 may be formed by a single elongated opening extending peripherally or by a plurality of small openings arranged peripherally and fluidly connected to respective supply nozzles 42.

Referring to FIGS. 9 and 10, the connecting channels 144 are defined below the air inlet 142 so that they oppose to the lower openings of the first channels 120. In this embodiment, nine channels 144 are formed in a region 302 extending peripherally about 120 degrees and including the region 300 in which the air inlet 142 is positioned. The connecting channels 144 are partitioned by vertical walls 146. As can be seen, each of the connecting channels 144 is a concaved portion 151 that is defined by three walls; one side surface of the vertical wall 146 located on the upstream side with respect to the rotational direction 44 of the rotor 102 (first surface or upstream surface 148), another side surface of the opposing vertical wall 146 located on the downstream side of the previous vertical wall (second surface or downstream surface 150), and a surface (third surface 152) positioned between the opposing side surfaces and curved downwardly and inwardly (see FIG. 7). An upper end opening 154 of the channel 144, which is defined by the upper edges of three surfaces 148, 150, and 152, is connected to the bottom openings of the first channels 120. Also, An inner end opening 156, which is defined by the inner edges of three surfaces 148, 150, and 152, is connected to the outer peripheral opening of the second channel 132.

Preferably, as best shown in FIG. 9, corners or connecting portions between the upstream and downstream surfaces 148 and 150 and the neighboring curved surface 152 are curved in order to minimize the frictional force to the air. More preferably, a radius of curvature of the curved corner is 0.1 mm or more.

As best shown in FIG. 9, each of the vertical walls 146 is extended diagonally in the rotational direction 44 of the rotor 102 so that it defines a certain angle with a line passing across the central axis 22. In this embodiment, an angle β formed by the vertical wall 146 (e.g., upstream surface 148) and the tangential line extending across the innermost edge of the upstream surface is determined to about 45–60 degrees.

Also, as shown in FIGS. 9 and 10, the guide ring 140 has an outlet opening or outlet 158 formed therein so that, when the rotor 102 is placed in the guide ring 140, the outlet 158 opposes to the second channels 132. Thereby, when the guide ring 140 is mounted in the chamber 54, the outlet 158 opposes to the discharge passage 32 so that the air from the second channels 132 is discharged through the outlet 158 into the discharge passage 32.

Preferably, the guide ring 140 as well as the lower casing 110 and upper guide ring 90 is manufactured by the conventional machining techniques, such as end mill and EDM (electric discharge machining). Also, since each of the connecting channels 144 formed in the guide ring 140 is defined only by planes (i.e., surfaces 148, 150, and 152) extending in the axial direction, they can be accessed and then machined from one direction, i.e., from above, through the upper opening in FIG. 10. Contrary to this, the inner housing used in the conventional air-driven rotating and cutting device has one or more walls each defined at least in part by a surface extending substantially perpendicular to the central axis. As a result, disadvantageously the working machine should be tilted or angled in various directions during the manufacturing thereof.

As shown in FIG. 1, in the cutting operation of the tooth by using the handpiece so constructed, a suitable cutting tool 72 is selected and then attached to the tool holder 74. In this state, the pressurized air is supplied from the pressurized-air source not shown through the supply tube 15 into the main supply passage 30. The air is then distributed from the main supply passage 30 through or not through the intermediate supply passages 36 and 38 into the supply nozzles 42 where it is accelerated by the existence of the reducing portions 52. The accelerated air is ejected through the inlet 142 of the guide ring 140 in the downstream direction with respect to the rotational direction 44 of the rotor 102, and in the direction perpendicular to the rotational axis 22. Then, as the rotor 102 rotates, the air is fed into each air channel 120, through its outward peripheral opening, that opposes to and passes by the inlet 142, which forces the rotor 102 to rotate in the rotational direction 44 (see FIG. 8).

Referring to FIGS. 7, 9, and 10, the pressurized air in the first channel 120 between the first turbine blades 112 flows downward. Then, when each channel 120 reaches and opposes the connecting channels 144 of the guide ring 140 according to the rotation of the rotor 102, the air flows through the bottom opening of the channel 120 into the connecting channels 144. The air in the connecting channel 144 flows downward and then inward along the vertical walls 146 and the curved wall 152 into the second channels 132 of the rotor 102. Then, the air in the second channel 132 is guided downward by the opposing second turbine blades 124 and the inner curved surface 130 and then discharged through the outlet 158 into the discharge passage 32. Finally, the air in the discharge passage 32 is fed into the tube 15 through which it is discharged into the atmosphere.

According to the above-described handpiece 10, since the first turbine blades 112 of the rotor 102 are curved in the rotational direction 44 as shown in FIG. 8, the pressurized air fed into the first channels 120 acts most effectively on the first turbine blades 112. This ensures the high speed and high torque rotation of the rotor.

Also, the second turbine blades 124 are extended in the axial direction 22, which results in a small reduction of the increase of the rotational number and the torque derived therefrom. However, the reduction is substantially small, which still ensures the high speed and high torque rotation of the rotor. The reduction of the torque can be compensated substantially by the increasing the number of the connecting channels 144 in the guide ring 140. Therefore, according to the present invention, the handpiece which is simple in structure and thereby easy to be manufactured than the conventional handpiece having the rotor disclosed in JP 10-23746 (A), in particular in FIGS. 14 and 15 thereof, can be obtained. Also obtained is the handpiece in which rotor rotates a bit slower than that in the conventional handpiece without any reduction in torque.

Figure 11:
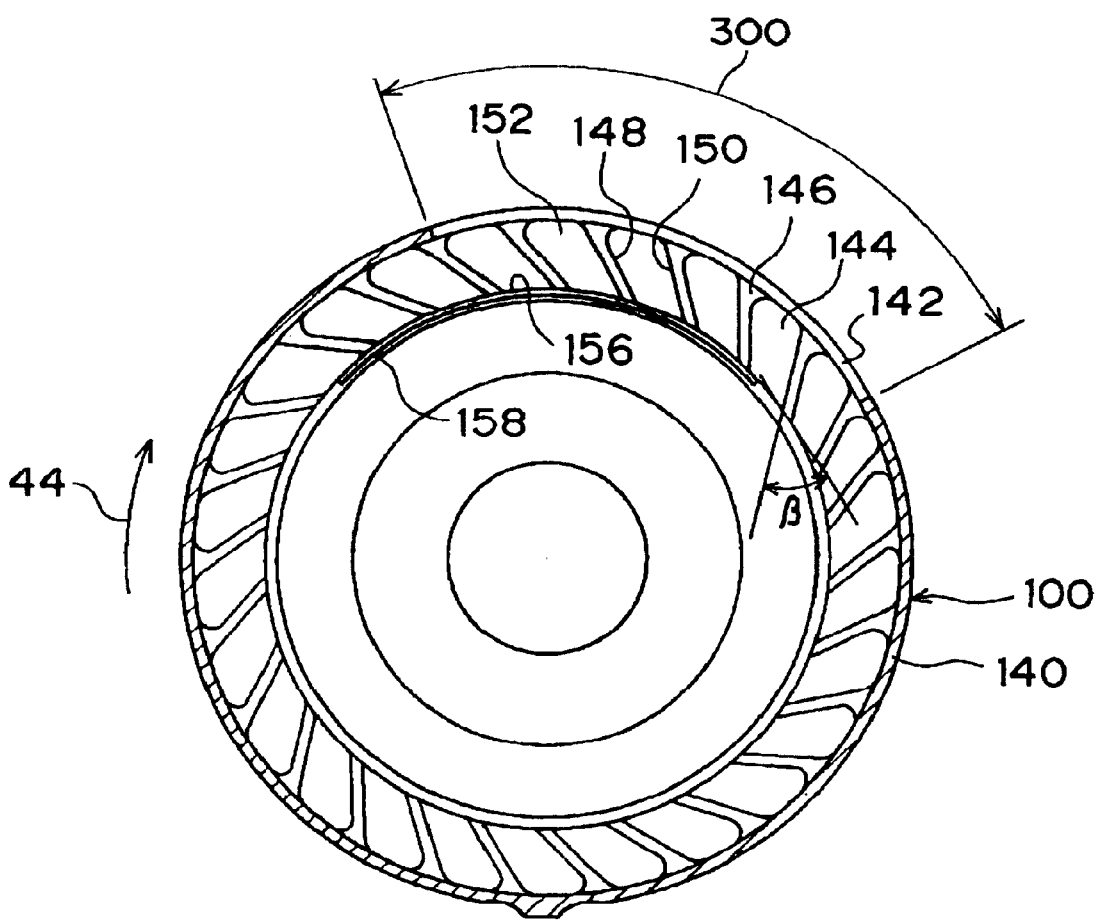
FIG. 11 is a cross sectional view of another guide ring according to another embodiment.

FIG. 11 shows a modification of the guide ring, in particular the connecting channels. The guide ring 140 of the modification has more connecting channels 144 in its entire peripheral area. With this guide ring 140, the rotor 102 ensures substantially the same torque as the conventional one and less rotational number than the first embodiment.

Figure 12:
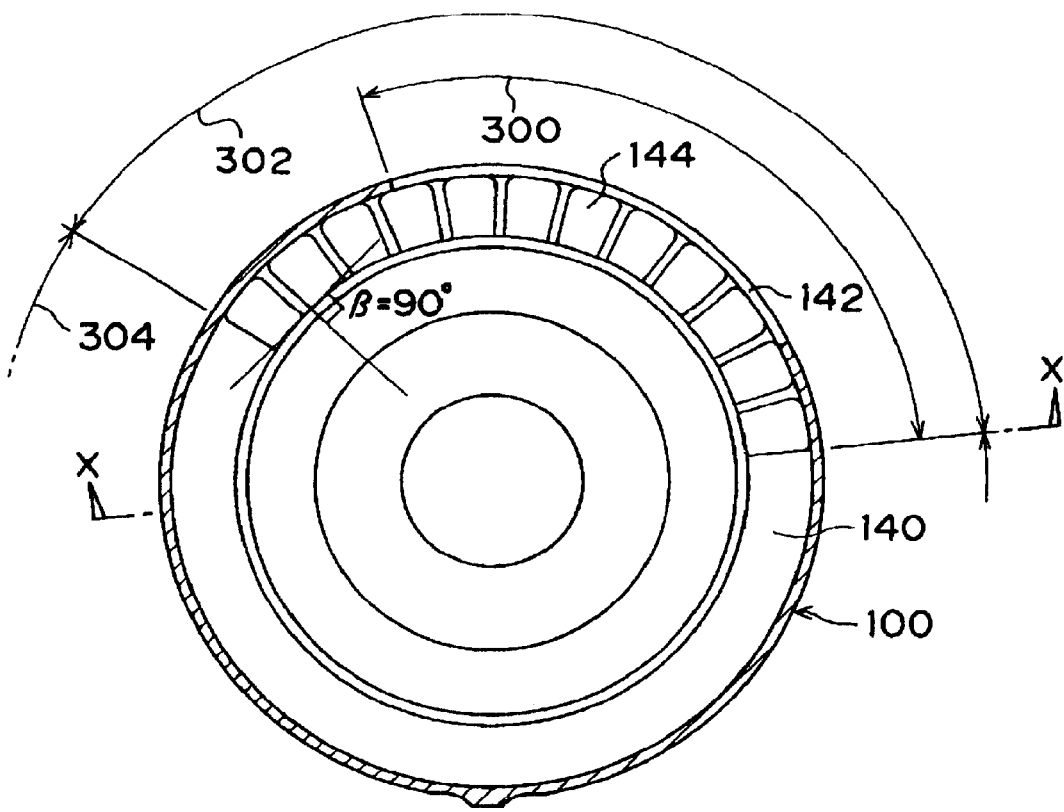
FIG. 12 is a cross sectional view of the guide ring for use with the handpiece in FIG. 2, taken along a line XI—XI in FIG. 13.
Figure 13:
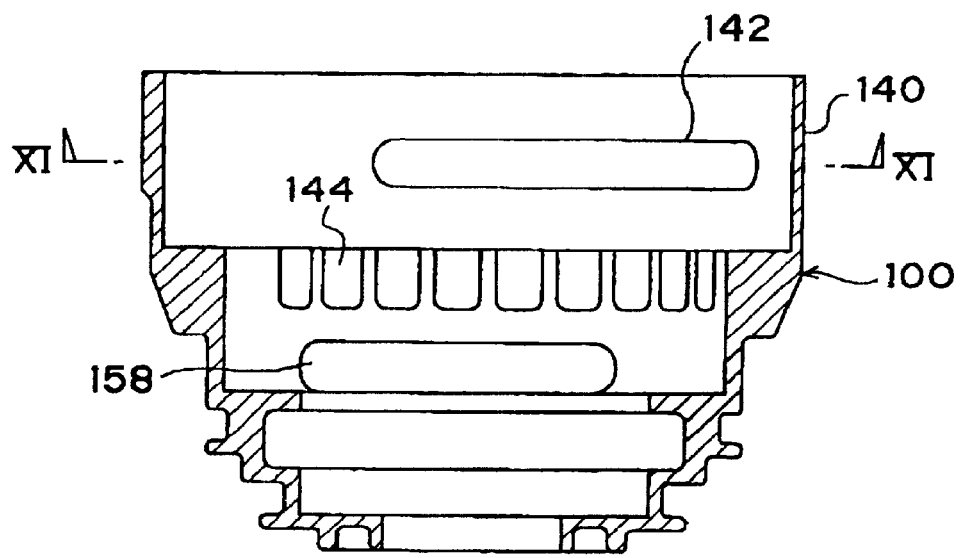
FIG. 13 is a cross sectional view of a guide ring for use with the handpiece in FIG. 2, taken along a line XII—XII in FIG. 12.

The angle β defined by the vertical wall 146 in the guide ring 140 and its tangential line has a close relationship with the rotational number and the torque of the rotor 102. For example, the decrease (increase) of the angle β increases (decreases) the rotational number. In theory, if the angle β is equal to or more than 90 degrees, the rotational number and the torque of the rotor is less than those derived only by the first turbine blades 112. Therefore, in order to decrease the rotational number without any reduction of the torque, as shown in FIGS. 12 and 13, each of the vertical walls 146 of the guide ring 140 is preferably oriented directly to the central axis 22. Further reduction of the rotational number of the rotor can be attained by setting the angle β more than 90 degrees.

Figure 14:
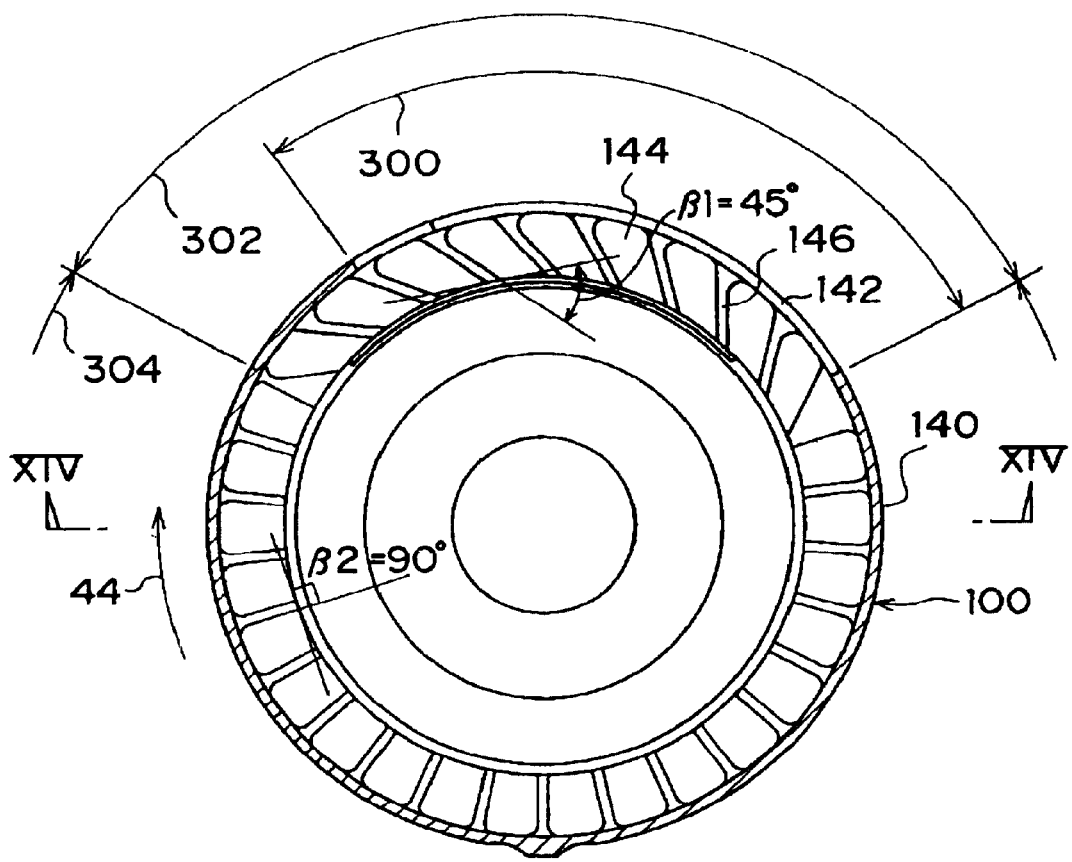
FIG. 14 is a cross sectional view of a guide ring for use with the handpiece in FIG. 2, taken along a line XIII—XIII in FIG. 15.
Figure 15:
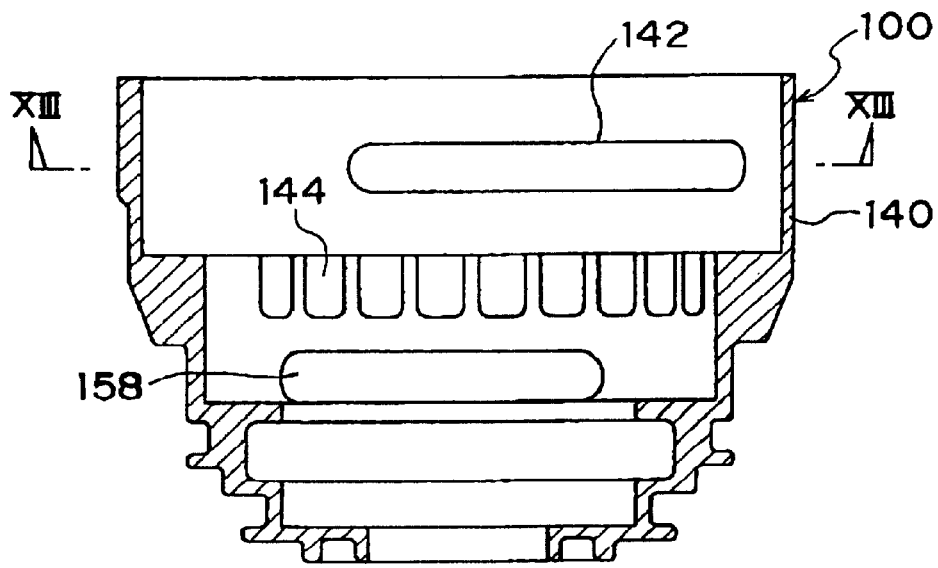
FIG. 15 is a cross sectional view of a guide ring for use with the handpiece in FIG. 2, taken along a line XIV—XIV in FIG. 14.
Figure 16:
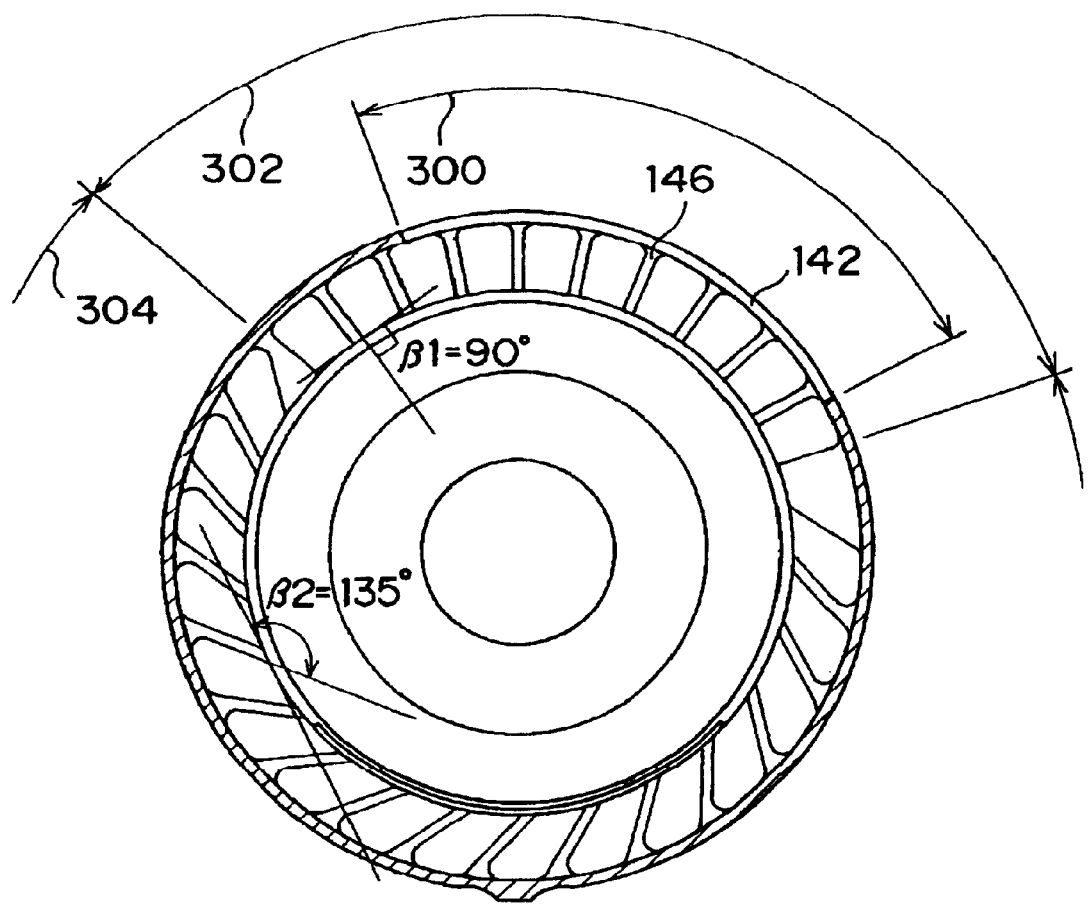
FIG. 16 is a cross sectional view of another guide ring.

To reduce the rotational number without any reduction of the torque, as shown in FIGS. 14 and 15, the vertical walls 146 in the region 302, including the region 300 in which the inlet 142 is defined, are oriented in the rotational direction so that they define an angle β1 of about 45 degrees, for example, with respective tangential lines thereof and another vertical walls in the remaining region 304 are oriented toward the central axis 22 so that they define an angle of β2 of about 90 degrees with respective tangential lines thereof. FIG. 16 shows another modification in which the angles β1 and β2 have 90 and 135 degrees, respectively. In those instances, even when the rotational number of the rotor is decreased due to the cutting load, a major part of the air flows through region 300, which prevents the significant reduction of the torque. On the other hand, when the rotor bears no or small load, the air flows not only through the region 300 but also through the region 302, which slightly reduces the rotational number of the rotor without any reduction of the torque.

II. Second Embodiment

Figure 19:
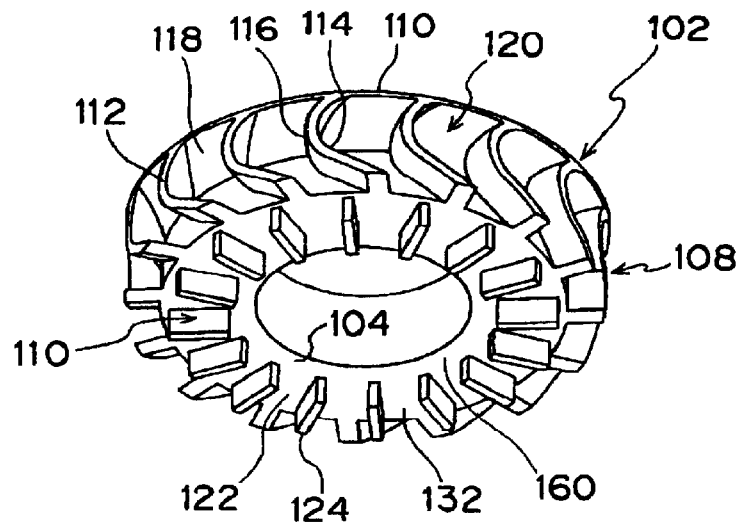
FIG. 19 is a perspective view of the rotor for use with the handpiece shown in FIG. 17.
Figure 20:
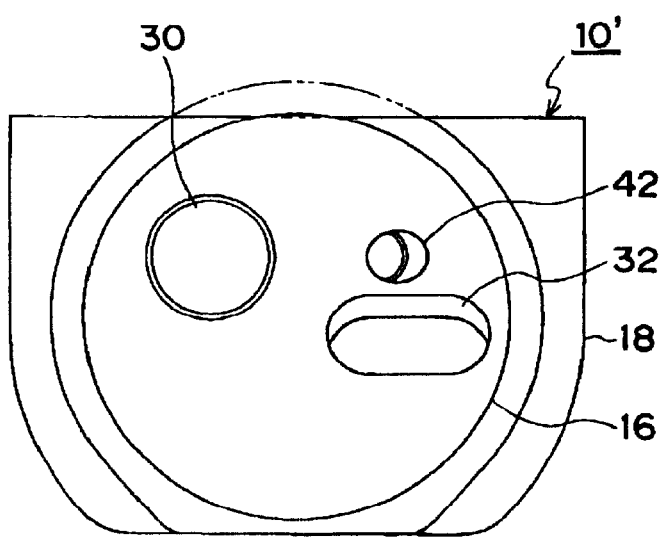
FIG. 20 is a rear side elevational view of the head of the handpiece shown in FIG. 17.

FIGS. 17 to 20 show another air-driven rotating and cutting device according to the second embodiment of the present invention. In this cutting device 10', as best shown in FIG. 19 the second channel 132 defined between the opposing second turbine blades 124 has inward and outward openings. Also, the second turbine blades 124 arranged in an annular fashion define therein an annular air passage 160 (fourth passage) around the tool holder 74. Namely, the second turbine blades 124 are formed in the bottom surface of the hub 106 of the first turbine wheel 108.

Figure 17:
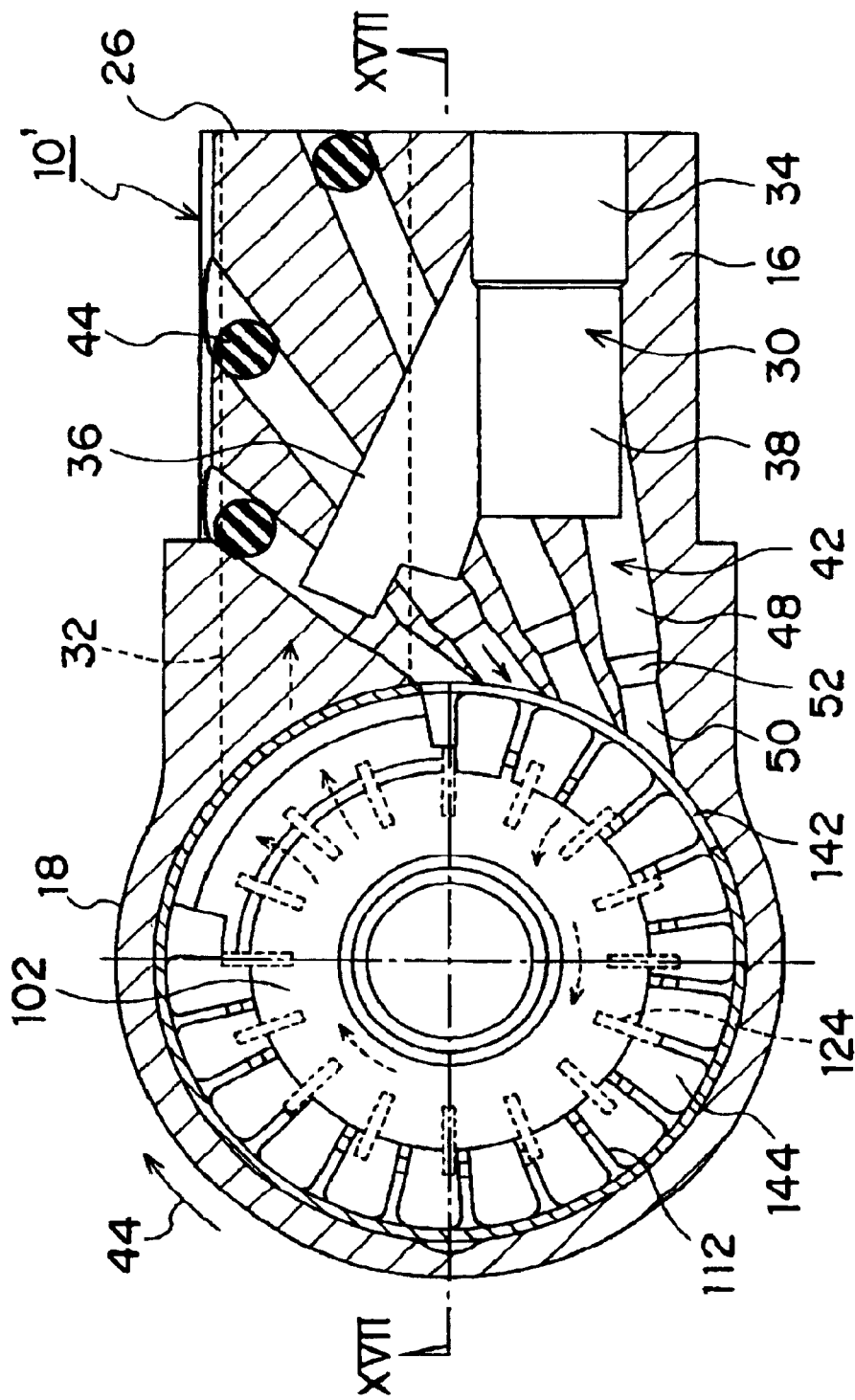
FIG. 17 is a cross sectional view of the handpiece according to the second embodiment of the present invention.
Figure 18:
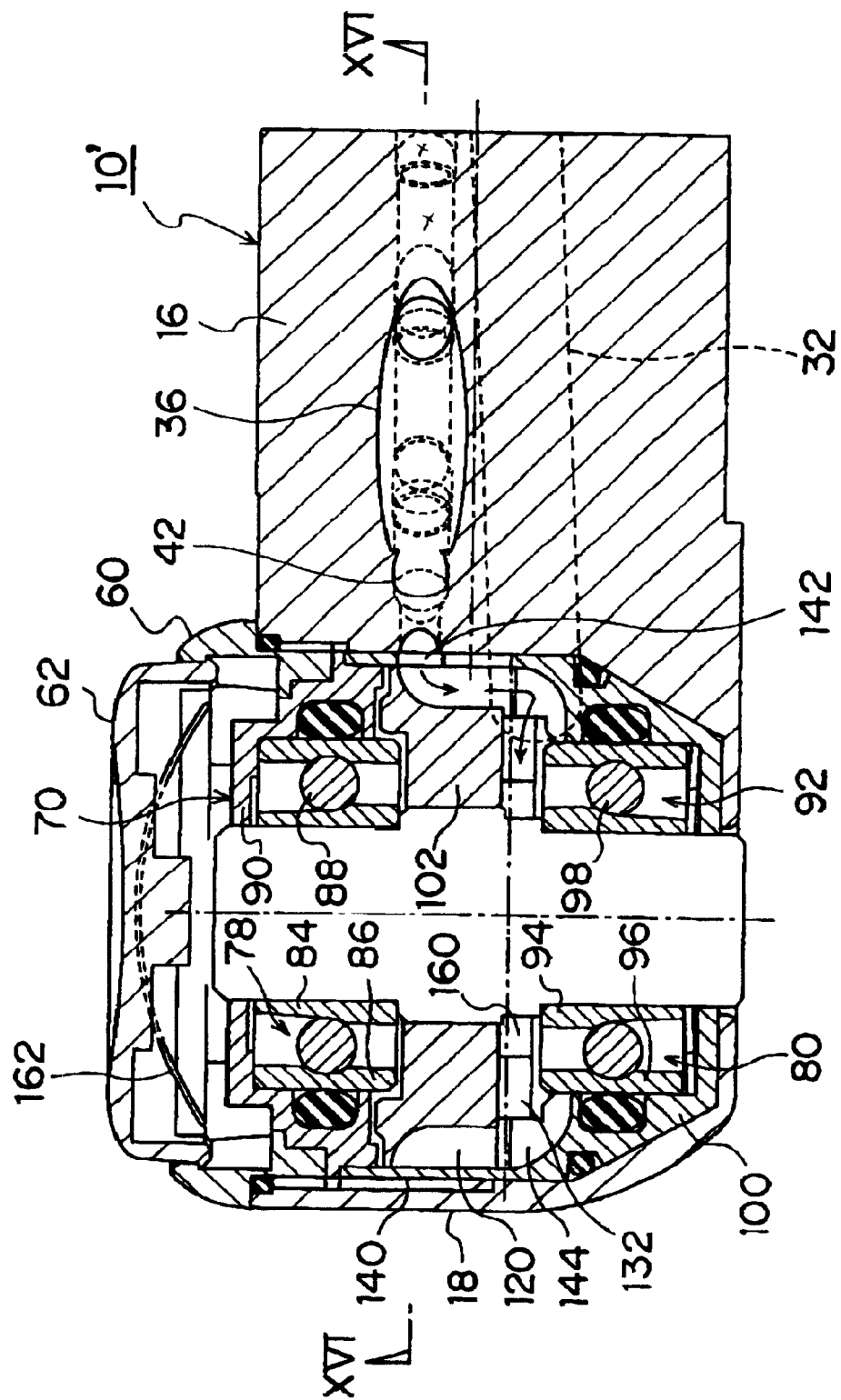
FIG. 18 is a cross sectional view taken along a line XVII—XVII in FIG. 17.

Although as shown in FIGS. 17 and 19 the second turbine blades 124 are directed toward the rotational axis 22 of the rotor, they may be oriented diagonally. For example, in order to increase the torque, the inward edges of the blades 124 are shifted against the rotational direction and, on the other hand, in order to decrease the rotational number, they are shifted in the rotational direction.

Although it can reduce the manufacturing ability of the rotor, the turbine blades may be curved in the rotational direction, which smoothes the air flow along the blades and thereby increase the torque. Note that reference numeral 162 indicates a leaf spring for holding the cap 60 in position.

With the air-driven rotating cutting device, the air is supplied from the passage 30 through the first channels 120, the connecting channels 144 and the second channels 132 into the fourth channel 160. In the fourth channel 160 the air moves in the rotational direction 44 of the rotor 102 and then flows again through the channel 132 into the discharge passage 32. In particular, with respect to the rotational direction of the rotor 102, for example in the clockwise direction in FIG. 17, the air from the supply passage 30 is ejected into the first channels 120 in the region extending from about one to three o'clock. On the other hand, the air from the fourth passage 160 is discharged into the discharge passage 32 also in the region from about one to three o'clock. This means that the air fed into the channels travels substantially full circle around the central axis.

In addition, as described above the air moves past the third passages 132 twice in the chamber 54. This brakes the rotor 102, which reduces the rotational number of the rotor by, for example in the dental handpiece, about 10,000 to 50,000 rpm. This allows the rotor as well as the cutting device to be small-sized in the axial direction.

Although components of the cutting device are usually made of steel unless any description has been made to the material thereof in the above, they may be made of other materials such as nonferrous metal and plastic provided that they provide any harmful effect (e.g., reduction in durability) to the components.

What is claimed is:

1. An air-driven rotating and cutting device, which comprises a rotor having a rotational axis and detachably holding a cutting tool along said rotational axis, said rotor being formed with first and second turbine wheels, said first and second turbine wheels being formed with first and second blades, respectively, each of said first blades defining a first channel with adjacent first blade therebetween and each of said second blade defining a second channel with adjacent second blade therebetween; and a housing having a cylindrical casing made from a single member for receiving said rotor for rotation about said rotational axis, said casing having channels for fluidly connecting said first and second channels, so that an air is guided from said first channels through said connecting channels to said second channels to rotate said rotor, wherein each of said connecting channels is defined by an opening opened toward a direction parallel to said rotational axis and a surface portion formed by extending said opening to a direction parallel to said rotational axis so that every part of said surface portions is accessible from said direction.

2. A device in accordance with claim 1, wherein said second blades provided in said second turbine wheel are extended parallel to said rotational axis.

3. A device in accordance with claim 1, wherein said surface portion of said connecting channel has a peripheral surface extending from said opening parallel to said rotational axis and curved radially inwardly toward said rotational axis, and a pair of opposing surfaces extended parallel to said rotational axis and positioned on opposite sides of said peripheral surface.

4. A device in accordance with claim 3, wherein said opposing surfaces are extended radially from said rotational axis.

5. A device in accordance with claim 3, wherein said opposing surfaces are angled with a line that crosses said rotational axis.

6. The air-driven rotating and cutting device according to claim 1, wherein, said second turbine blades define a third channel extending peripherally around said rotational axis.

7. An air-driven rotating and cutting device, which comprises a rotor having a rotational axis and detachably holding a cutting tool along said rotational axis, said rotor being formed with first and second turbine wheels, said first and second turbine wheels being formed with first and second blades, respectively, each of said first blades defining a first channel with adjacent first blade therebetween and each of said second blade defining a second channel with adjacent second blade therebetween; and a housing having a cylindrical casing made from a single member for receiving said rotor for rotation about said rotational axis, said casing having channels for fluidly connecting said first and second channels, so that an air is guided from said first channels through said connecting channels to said second channels to rotate said rotor;

wherein each of said connecting channels is defined by an opening opened toward a direction parallel to said rotational axis and a surface portion formed by extending said opening to a direction parallel said rotational axis so that every part of said surface portions is accessible from said direction;

said surface portion of said connecting channel has a peripheral surface extending from said opening parallel to said rotational axis and curved radially inwardly toward said rotational axis, and a pair of opposing surfaces extended parallel to said rotational axis and positioned on opposite sides of said peripheral surface; and a connecting portion of said peripheral and opposing surfaces is curved.

8. A device in accordance with claim 7, wherein said curved connecting portion has a radius curvature of 0.1 mm or more.

9. The air-driven rotating and cutting device according to claim 1,
wherein a peripheral region in which said connecting channels are formed is greater than that in which an inlet through which said air is ejected against said first blades exists.

10. A device in accordance with claim 9, wherein said peripheral region of said connecting channels is extended in an entire peripheral area of said housing.

11. A device in accordance with claim 9,
wherein said peripheral region in which said connecting channels are formed includes a first region in which said inlet through which said air is ejected against said first blades and a second region outside said first region,
wherein a surface portion of said connecting channel has a peripheral surface extending from said opening parallel to said rotational axis and curved radially inwardly toward said rotational axis, and a pair of opposing surfaces extended parallel to said rotational axis and positioned on opposite sides of said peripheral surface, and
wherein each of said opposing surfaces in said first region defines a first angle with a line that crosses said rotational axis and each of said opposing surfaces in said second region defines a second angle with said line, said second angle being different from said first angle.

12. A device in accordance with claim 9,
wherein said peripheral region in which said connecting channels are formed includes a first region including said inlet through which said air is ejected against said first blades and a second region outside said first region,
wherein said surface portion of said connecting channel has a peripheral surface extending from said opening parallel to said rotational axis and curved radially inwardly toward said rotational axis, and a pair opposing surfaces extended parallel to said rotational axis and positioned on opposite sides of said peripheral surface, and
wherein each of said opposing surfaces in said first region is directed so that a line extended inwardly from an innermost end thereof toward said rotational axis defines a first angle with a tangential line extending in a rotational direction of said rotor from said innermost end, and each of said opposing surfaces in said second region is directed so that a line extended inwardly from an innermost end thereof toward said rotational axis defines a second angle with a tangential line extending in a rotational direction of said rotor from said innermost end, said second angle being greater than said first angle.

13. An air-driven rotating and cutting device, comprising:
a rotor having an annular hub extending around a rotational axis of said rotor and detachably holding a cutting tool in said annular hub, said hub being farmed with first and second turbine wheels, said first and second turbine wheels being formed with first and second blades, respectively, each of said first blades defining a first channel wit adjacent first blade therebetween and each of said second blade defining a second channel with adjacent second blade therebetween, each of said second blades being extended parallel to said rotational axis; and
a housing having a cylindrical casing made from a single member for receiving said rotor for rotation about said rotational axis, said casing having channels for fluidly connecting said first and second channels, so that an air is guided from said first channels through said connecting channels to said second channels to rotate said rotor,
wherein each of said connecting channels is defined by an opening opened toward a direction parallel to said rotational axis and a surface portion formed by extending said opening to a direction parallel to said rotational axis so that every part of said surface portions is accessible from said direction.

14. An air-driven rotating and cutting device, comprising:
a rotor having an annular hub extending around a rotational axis of said rotor and detachably holding a cutting tool in said annular hub, said hub being formed with first and second turbine wheels, said first and second turbine wheels being formed with first and second blades, respectively, each of said first blades defining a first channel with adjacent first blade therebetween and each of said second blade defining a second channel with adjacent second blade therebetween, said second turbine blades being formed in one end surface of said annular hub; and
a housing having a cylindrical casing made from a single member for receiving said rotor for rotation about said rotational axis, said casing having channels for fluidly connecting said first and second channels, so that an air is guided from said first channels through said connecting channels to said second channels to rotate said rotor,
wherein each of said connecting channels is defined by an opening opened toward a direction parallel to said rotational axis and a surface portion formed by extending said opening to a direction parallel to said rotational axis so that every part of said surface portions is accessible from said direction.

15. An air-driven rotating and cutting device, comprising:
a rotor having an annular hub extending around a rotational axis of said rotor and detachably holding a cutting tool in said annular hub, said hub being formed with first and second turbine wheels, said first and second turbine wheels being formed with first and second blades, respectively, each of said first blades defining a first channel with adjacent first blade therebetween and each of said second blade defining a second channel with adjacent second blade therebetween, said second turbine blades being formed in one end surface of said annular hub; and
a housing having a cylindrical casing made from a single member for receiving said rotor for rotation about said rotational axis, said casing having channels for fluidly connecting said first and second channels, so that an air is guided from said first channels through said connecting channels to said second channels to rotate said rotor,
wherein each of said connecting channels is defined by an opening opened toward a direction parallel to said rotational axis and a surface portion formed by extending said opening to a direction parallel to said rotational axis so that every part of said surface portions is accessible from said direction; and
each of said second channels is opened at inward and outward ends thereof.

16. An air-driven rotating and cutting device, comprising:
a rotor having a rotational axis and detachably holding a cutting tool along said rotational axis, said rotor being formed with first and second turbine wheels, said first and second turbine wheels being formed with first and second channels, respectively; and a head having a housing portion and a coupling portion, wherein said housing portion having a cylindrical casing made from a single member for receiving said rotor for rotation about said rotational axis, said casing having channels for fluidly connecting said first and second channels, so tat an air is guided from said first channels through said connecting channels to said second channels to rotate said rotor, wherein each of said connecting channels is defined by an opening opened toward a direction parallel to said rotational axis and a surface portion formed by extending said opening to a direction parallel to said rotational axis so that every part of said surface portions is accessible from said direction, and wherein said coupling portion having a main air supply passage extending parallel to a central axis of said coupling portion and nozzles fluidly connected with said main air supply passage so that said air supplied from said main air supply passage is ejected to said first turbine wheel in a direction perpendicular to said rotational axis of said rotor.

17. A device in accordance with claim 16, wherein said coupling portion of said head further comprises one or more intermediate passages for connecting between said main air supply passage and said nozzles.

18. A device in accordance with claim 17, wherein an effective cross sectional area of said intermediate passages is greater than that of said nozzles.

19. A device in accordance with claim 17, wherein each of said nozzles has a portion where a cross sectional area thereof is reduced.

20. A device in accordance with claim 19, wherein said reduced portion is tapered.

21. A device in accordance wit claim 19, wherein said nozzles are positioned so that each of said nozzle defines a greater angle with said central axis of said coupling portion than another nozzle located on a downstream side with respect to a rotational direction of said rotor.

* * * * *